US00PP24252P2

(12) United States Plant Patent
van Nijnatten

(10) Patent No.: US PP24,252 P2
(45) Date of Patent: Feb. 18, 2014

(54) LILAC PLANT NAMED 'PINK PERFUME'

(50) Latin Name: ***Syringa meyeri*×*Syringa microphylla***
Varietal Denomination: Pink Perfume

(76) Inventor: Andre Franciscus van Nijnatten, Zundert (NL)

( * ) Notice: Subject to any disclaimer, the term of this patent is extended or adjusted under 35 U.S.C. 154(b) by 145 days.

(21) Appl. No.: 13/385,431

(22) Filed: Feb. 17, 2012

(51) Int. Cl.
*A01H 5/00* (2006.01)

(52) U.S. Cl.
USPC ..... Plt./248

(58) Field of Classification Search
USPC ..... Plt./248
See application file for complete search history.

(56) References Cited

PUBLICATIONS

Pluto: Plant Variety Database 201302 of UPOV-ROM, retrieved on Aug. 15, 2013. Retrieved from the Internet at<http://www.upov.int/pluto/en/index.jsp>, for *Syringa* 'Pink Perfume', one page.*

* cited by examiner

*Primary Examiner* — June Hwu
(74) *Attorney, Agent, or Firm* — C. A. Whealy

(57) ABSTRACT

A new and distinct cultivar of Lilac plant named 'Pink Perfume', characterized by its relatively compact, upright and somewhat outwardly spreading plant habit; moderately vigorous growth habit; freely branching habit; freely flowering habit; large inflorescences with strongly fragrant pink-colored flowers that are not persistent; long and repeat flowering habit; and good cold hardiness.

2 Drawing Sheets

Botanical designation: *Syringa meyeri*×*Syringa microphylla.*

Cultivar denomination: 'PINK PERFUME'.

BACKGROUND OF THE INVENTION

The present invention relates to a new and distinct cultivar of Lilac plant, botanically known as *Syringa meyeri*×*Syringa microphylla* and hereinafter referred to by the name 'Pink Perfume'.

The new Lilac plant is a product of a planned breeding program conducted by the Inventor in Zundert, The Netherlands. The objective of the breeding program is to create new Lilac plants with fragrant flowers and repeat flowering habit.

The new Lilac plant originated from a cross-pollination conducted by the Inventor in 2000 of *Syringa meyeri* 'Palibin', not patented, as the female, or seed, parent with *Syringa microphylla* 'Superba', not patented, as the male, or pollen, parent. The new Lilac plant was discovered and selected by the Inventor during the summer of 2003 as a single flowering plant from within the progeny of the stated cross-pollination in a controlled environment in Zundert, The Netherlands.

Asexual reproduction of the new Lilac plant by softwood cuttings in a controlled greenhouse environment in Zundert, The Netherlands since 2004 has shown that the unique features of this new Lilac plant are stable and reproduced true to type in successive generations of asexual reproduction.

SUMMARY OF THE INVENTION

Plants of the new Lilac have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Pink Perfume'. These characteristics in combination distinguish 'Pink Perfume' as a new and distinct Lilac plant:

1. Relatively compact, upright and somewhat outwardly spreading plant habit.
2. Moderately vigorous growth habit.
3. Freely branching habit.
4. Freely flowering habit.
5. Large inflorescences with strongly fragrant pink-colored flowers that are not persistent.
6. Long and repeat flowering habit.
7. Good cold hardiness.

Plants of the new Lilac can be compared to plants of the female parent, 'Palibin'. Plants of the new Lilac differ primarily from plants of 'Palibin' in the following characteristics:

1. Plants of the new Lilac are larger than plants of 'Palibin'.
2. Plants of the new Lilac are more freely flowering and flower for a longer period of time than plants of 'Palibin'.
3. Plants of the new Lilac have larger inflorescences than plants of 'Palibin'.

Plants of the new Lilac can be compared to plants of the male parent, 'Superba'. Plants of the new Lilac differ primarily from plants of 'Superba' in the following characteristics:

1. Plants of the new Lilac are more compact than and not as open as plants of 'Superba'.
2. Plants of the new Lilac flower for a longer period of time than plants of 'Superba'.
3. Plants of the new Lilac have larger inflorescences than plants of 'Superba'.
4. Flowers of plants of the new Lilac were more fragrant than flowers of plants of 'Superba'.

Plants of the new Lilac can be also compared to plants of the *Syringa hybrida* 'Penda', disclosed in U.S. Plant Pat. No. 20,575. In side-by-side comparisons conducted in Grand Haven, Mich., plants of the new Lilac differed primarily from plants of 'Penda' in the following characteristics:

1. Plants of the new Lilac were more compact than and were not as open as plants of 'Penda'.
2. Plants of the new Lilac had larger inflorescences than plants of 'Penda'.
3. Flowers of plants of the new Lilac and 'Penda' differed in flower color as plants of 'Penda' had purple-colored flowers.

BRIEF DESCRIPTION OF THE PHOTOGRAPHS

The accompanying colored photographs illustrate the overall appearance of the new Lilac plant showing the colors as true as it is reasonably possible to obtain in colored reproductions of this type. Colors in the photographs may differ slightly from the color values cited in the detailed botanical description which accurately describe the colors of the new Lilac plant.

The photograph on the first sheet is a side perspective view of a flowering typical plant of 'Pink Perfume' grown in an outdoor nursery.

The photograph on the second sheet is a close-up view of a typical flowering plant of 'Pink Perfume'.

DETAILED BOTANICAL DESCRIPTION

The aforementioned photographs and following observations, measurements and values describe plants grown during the spring in an outdoor nursery in Grand Haven, Mich. under cultural practices which closely approximate commercial production. During the production of the plants, day temperatures ranged from 12° C. to 25° C. and night temperatures ranged from 4° C. to 14° C. Plants were five years old when the photographs and the description were taken. In the description, color references are made to The Royal Horticultural Society Colour Chart, 2001 Edition, except where general terms of ordinary dictionary significance are used.

Botanical classification: *Syringa meyeri*×*Syringa microphylla* 'Pink Perfume'.

Parentage:

*Female, or seed, parent.*—*Syringa meyeri* 'Palibin', not patented.

*Male, or pollen, parent.*—*Syringa microphylla* 'Superba', not patented.

Propagation:

*Type.*—By softwood cuttings.

*Time to initiate roots, summer.*—About 20 to 30 days at 15° C. to 20° C.

*Time to produce a rooted young plant, summer.*—About two months at 15° C. to 20° C.

*Root description.*—Fine, fibrous; greyed white in color.

*Rooting habit.*—Freely branching; dense.

Plant description:

*Plant form and growth habit.*—Perennial shrub; compact, upright and somewhat outwardly spreading plant habit; moderately vigorous growth habit.

*Branching habit.*—Freely branching habit, about ten primary branches each with about 35 lateral branches.

*Plant height.*—About 78.5 cm.

*Plant diameter* (*area of spread*).—About 87 cm.

Lateral branch description:

*Length.*—About 14.1 cm.

*Diameter.*—About 1.5 mm.

*Internode length.*—About 3.6 cm.

*Texture.*—Pubescent.

*Color.*—Close to 177A and N199B.

Foliage description:

*Arrangement.*—Opposite, simple.

*Length.*—About 3.3 cm.

*Width.*—About 2.8 cm.

*Shape.*—Broadly ovate.

*Apex.*—Acute.

*Base.*—Obtuse.

*Margin.*—Entire; somewhat undulate.

*Texture, upper surface.*—Smooth, glabrous.

*Texture, lower surface.*—Sparsely pubescent.

*Venation pattern.*—Pinnate.

*Color.*—Developing leaves, upper surface: Close to 146A. Developing leaves, lower surface: Close to 146B. Fully expanded leaves, upper surface: Close to 137B to 137C; venation, close to 146C. Fully expanded leaves, lower surface: Close to 146B; venation, close to 144A.

*Petiole.*—Length: About 8 mm. Diameter: About 1 mm. Texture, upper and lower surfaces: Smooth, glabrous. Color, upper and lower surfaces: Close to 146B, towards the base close to 177A.

Flower description:

*Flower arrangement and flowering habit.*—Single salverform flowers arranged and axillary terminal panicles; freely flowering habit with usually about 110 flowers per inflorescence; flowers face upright to slightly outwardly.

*Natural flowering season.*—Plants of the new Lilac flower repeatedly form spring to autumn in Grand Haven, Mich.; plants begin flowering about seven months after planting.

*Flower longevity.*—Flowers last for about ten days on the plant; flowers not persistent.

*Fragrance.*—Strongly fragrant; fragrance sweet and pleasant.

*Inflorescence height.*—About 10.1 cm.

*Inflorescence diameter.*—About 6.3 cm.

*Flower diameter.*—About 8 mm.

*Flower length* (*height*).—About 1.3 cm.

*Flower buds.*—Length: About 8 mm. Diameter: About 2 mm. Shape: Spatulate. Color: Close to 186B; towards the base, close to 186C.

*Petals.*—Quantity and arrangement: Single whorl of four petals; lower 80% of petals fused forming a narrow tube. Lobe length: About 1.5 mm. Lobe width: About 3 mm. Lobe shape: Narrowly oblanceolate. Apex: Acute. Margin: Entire. Texture, upper and lower surfaces: Smooth, glabrous. Color: When opening and fully opened, upper surface: Close to 63D; towards the margins, slightly lighter than 63D; color becoming closer to 63C with development. When opening and fully opened, lower surface: Close to 63C.

*Sepals.*—Quantity and arrangement: Single whorl of four sepals; fused towards the base forming a campanulate-shaped calyx. Length: About 2 mm. Width: About 0.8 mm. Apex: Acute. Margin: Entire. Texture, upper and lower surfaces: Pubescent. Color, upper and lower surfaces: Close to 146C flushed with close to 181B to 181C.

*Peduncles.*—Length: About 8.8 cm. Diameter: About 1 mm. Strength: Moderately strong. Texture: Smooth, glabrous. Color: Close to N200A.

*Reproductive organs.*—Androecium: Anther shape: Oblong. Anther length: About 2 mm. Anther color:

Close to 182B to 182C. Amount of pollen: Moderate. Pollen color: Close to 4A to 4B. Gynoecium: Pistil length: About 2 mm. Style length: About 1.5 mm. Style color: Close to N155A. Stigma appearance: Club-shaped. Stigma color: Close to 150D. Ovary: Close to 143B.

*Seeds and fruits.*—Seed and fruit development have not been observed on plants of the new Lilac.

Garden performance: Plants of the new Lilac have been observed to have good garden performance and to tolerate rain and wind. Plants of the new Lilac are hardy to USDA Hardiness Zone 4 and USDA Heat Zone 9.

Pathogen & pest resistance: Plants of the new Lilac have been observed to be tolerant to Mildew. Plants of the new Lilac have not been shown to be resistant to pests and other pathogens common to Lilac plants.

It is claimed:

1. A new and distinct Lilac plant named 'Pink Perfume' as illustrated and described.

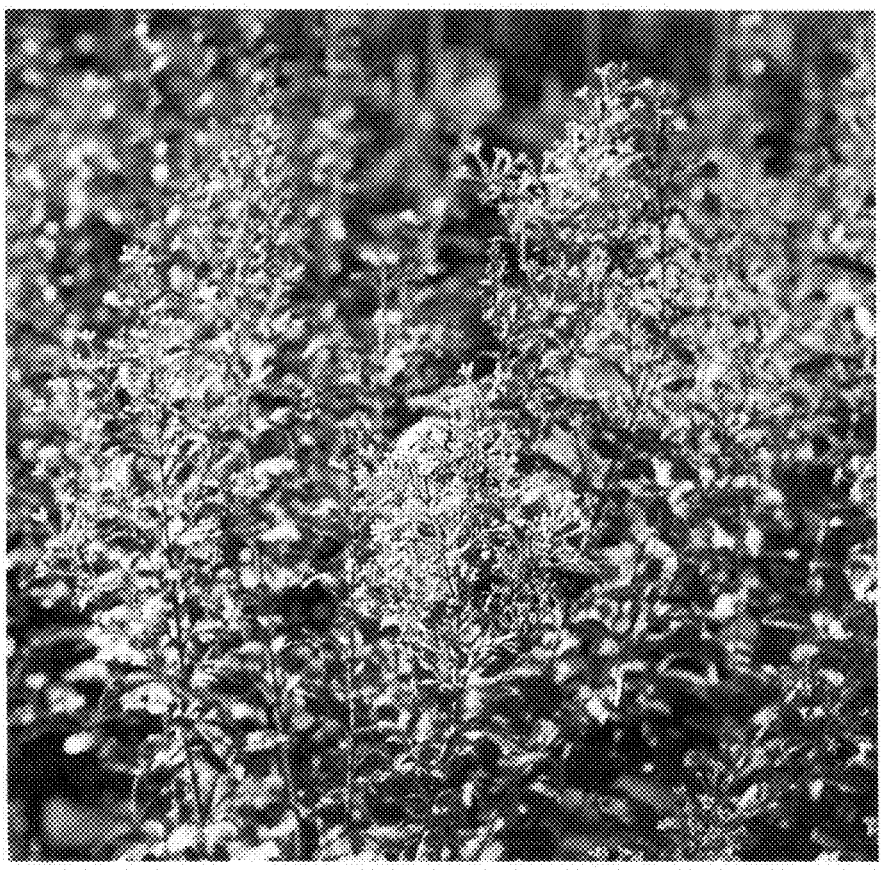

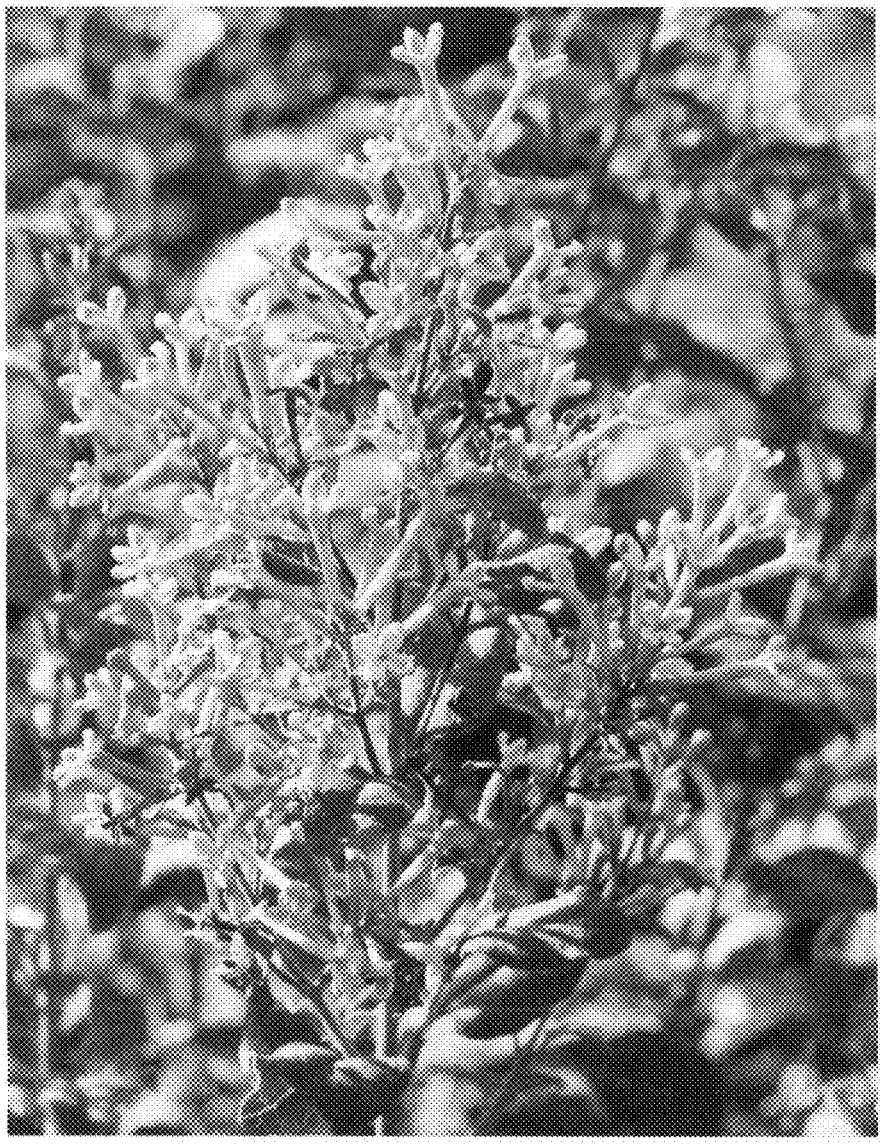

* * * * *